(12) United States Patent
Murase et al.

(10) Patent No.: US 10,070,780 B2
(45) Date of Patent: Sep. 11, 2018

(54) OPHTHALMOLOGIC PHOTOGRAPHING APPARATUS AND OPHTHALMOLOGIC PHOTOGRAPHING METHOD

(71) Applicant: NIDEK CO., LTD., Gamagori-shi, Aichi (JP)

(72) Inventors: Yuji Murase, Gamagori (JP); Yukihiro Higuchi, Gamagori (JP); Norimasa Satake, Gamagori (JP)

(73) Assignee: NIDEK CO., LTD., Gamagori-shi (JP)

( * ) Notice: Subject to any disclaimer, the term of this patent is extended or adjusted under 35 U.S.C. 154(b) by 82 days.

(21) Appl. No.: 15/183,288

(22) Filed: Jun. 15, 2016

(65) Prior Publication Data

US 2016/0287068 A1  Oct. 6, 2016

Related U.S. Application Data

(63) Continuation of application No. 13/782,379, filed on Mar. 1, 2013.

(30) Foreign Application Priority Data

Mar. 2, 2012 (JP) .................................. 2012-047174
Mar. 2, 2012 (JP) .................................. 2012-047176

(51) Int. Cl.
*A61B 3/14* (2006.01)
*A61B 3/00* (2006.01)
(Continued)

(52) U.S. Cl.
CPC ............ *A61B 3/0033* (2013.01); *A61B 3/005* (2013.01); *A61B 3/0025* (2013.01);
(Continued)

(58) Field of Classification Search
CPC ..... A61B 3/0033; A61B 3/0041; A61B 3/005; A61B 3/0058; A61B 3/102; A61B 3/12; A61B 3/14; A61B 3/145
(Continued)

(56) References Cited

U.S. PATENT DOCUMENTS 6,158,864 A  12/2000  Masuda et al.
7,306,336 B2  12/2007  Akita et al.
(Continued)

FOREIGN PATENT DOCUMENTS

EP  2 184 006 A1  5/2010
EP  2 347 701 A1  7/2011
(Continued)

OTHER PUBLICATIONS

Jun. 25, 2013 Extended European Search Report issued in EP Patent Application No. 13157444.4.
(Continued)

*Primary Examiner* — Nicholas R Pasko
(74) *Attorney, Agent, or Firm* — Oliff PLC

(57) ABSTRACT

An ophthalmologic photographing apparatus includes: a photographing optical system that includes a scanning unit for scanning an examinee's eye with measurement light to obtain a tomographic image of the examinee's eye; an observing optical system that includes a light-receiving device for receiving reflected light from the examinee's eye to obtain a moving image of a front image of the examinee's eye based on a light-receiving signal from the light-receiving device; a display controller for displaying the front image acquired by the observing optical system in a still state on a monitor as well as enabling setting of a capturing position of the tomographic image, the setting using the front image; and a drive controller for controlling the
(Continued)

scanning unit to acquire the tomographic image in accordance with the capturing position.

6 Claims, 5 Drawing Sheets

(51) Int. Cl.
 *A61B 3/10* (2006.01)
 *A61B 3/12* (2006.01)
(52) U.S. Cl.
 CPC ............ *A61B 3/0041* (2013.01); *A61B 3/102* (2013.01); *A61B 3/1225* (2013.01); *A61B 3/145* (2013.01)
(58) Field of Classification Search
 USPC ....... 351/206, 208, 209, 210, 211, 212, 246; 600/425
 See application file for complete search history.

(56) References Cited

U.S. PATENT DOCUMENTS

| | | | |
|---|---|---|---|
| 7,510,282 B2 | 3/2009 | Ueno et al. | |
| 7,641,338 B2* | 1/2010 | Fukuma | A61B 3/102 351/206 |
| 7,768,652 B2 | 8/2010 | Everett | |
| 7,784,942 B2 | 8/2010 | Maeda et al. | |
| 7,794,083 B2 | 9/2010 | Tsukada et al. | |
| 7,980,696 B1 | 7/2011 | Taki et al. | |
| 8,025,402 B2 | 9/2011 | Ueno | |
| 8,081,808 B2 | 12/2011 | Huang et al. | |
| 8,096,658 B2 | 1/2012 | Kikawa et al. | |
| 2005/0117118 A1* | 6/2005 | Miller | A61B 3/13 351/246 |
| 2008/0024721 A1 | 1/2008 | Ueno et al. | |
| 2008/0100612 A1 | 5/2008 | Dastmalchi et al. | |
| 2008/0204655 A1 | 8/2008 | Kikawa et al. | |
| 2008/0208525 A1* | 8/2008 | Kikawa | G01N 21/4795 702/172 |
| 2009/0285354 A1 | 11/2009 | Hirose et al. | |
| 2010/0110172 A1* | 5/2010 | Satake | A61B 3/102 348/78 |
| 2010/0149489 A1* | 6/2010 | Kikawa | A61B 3/102 351/206 |
| 2011/0149244 A1* | 6/2011 | Yamada | A61B 3/1241 351/206 |
| 2011/0205490 A1 | 8/2011 | Murata et al. | |
| 2011/0234785 A1* | 9/2011 | Wanda | A61B 3/12 348/78 |
| 2011/0299037 A1 | 12/2011 | Ueno | |
| 2012/0002164 A1 | 1/2012 | Yamamoto et al. | |
| 2012/0249961 A1 | 10/2012 | Muto | |
| 2012/0253183 A1 | 10/2012 | Muto | |
| 2013/0088686 A1 | 4/2013 | Graziano et al. | |
| 2013/0188130 A1 | 7/2013 | Inoue | |
| 2014/0111767 A1 | 4/2014 | Murase | |

FOREIGN PATENT DOCUMENTS

| | | |
|---|---|---|
| EP | 2 404 545 A2 | 1/2012 |
| JP | 2008-029467 A | 2/2008 |
| JP | 2008-289579 A | 12/2008 |

OTHER PUBLICATIONS

Dec. 21, 2015 Office Action issued in U.S. Appl. No. 13/782,379.
Jul. 17, 2015 Office Action issued in U.S. Appl. No. 13/782,379.
Mar. 26, 2015 Office Action issued in U.S. Appl. No. 13/782,379.
Oct. 2, 2014 Office Action issued in U.S. Appl. No. 13/782,379.
Aug. 12, 2014 Office Action issued in U.S. Appl. No. 13/782,379.

* cited by examiner

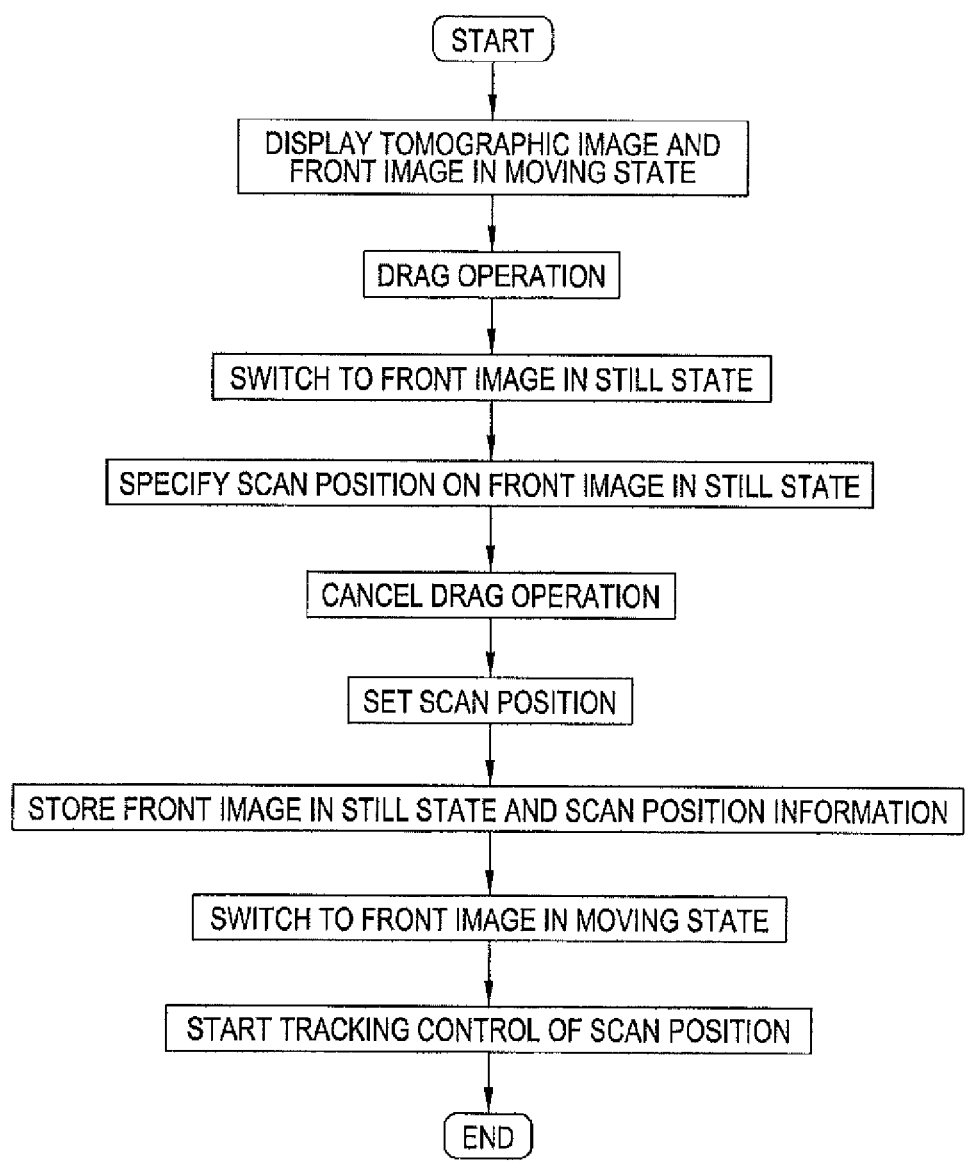

SCAN CENTER POSITION

SCAN CENTER POSITION

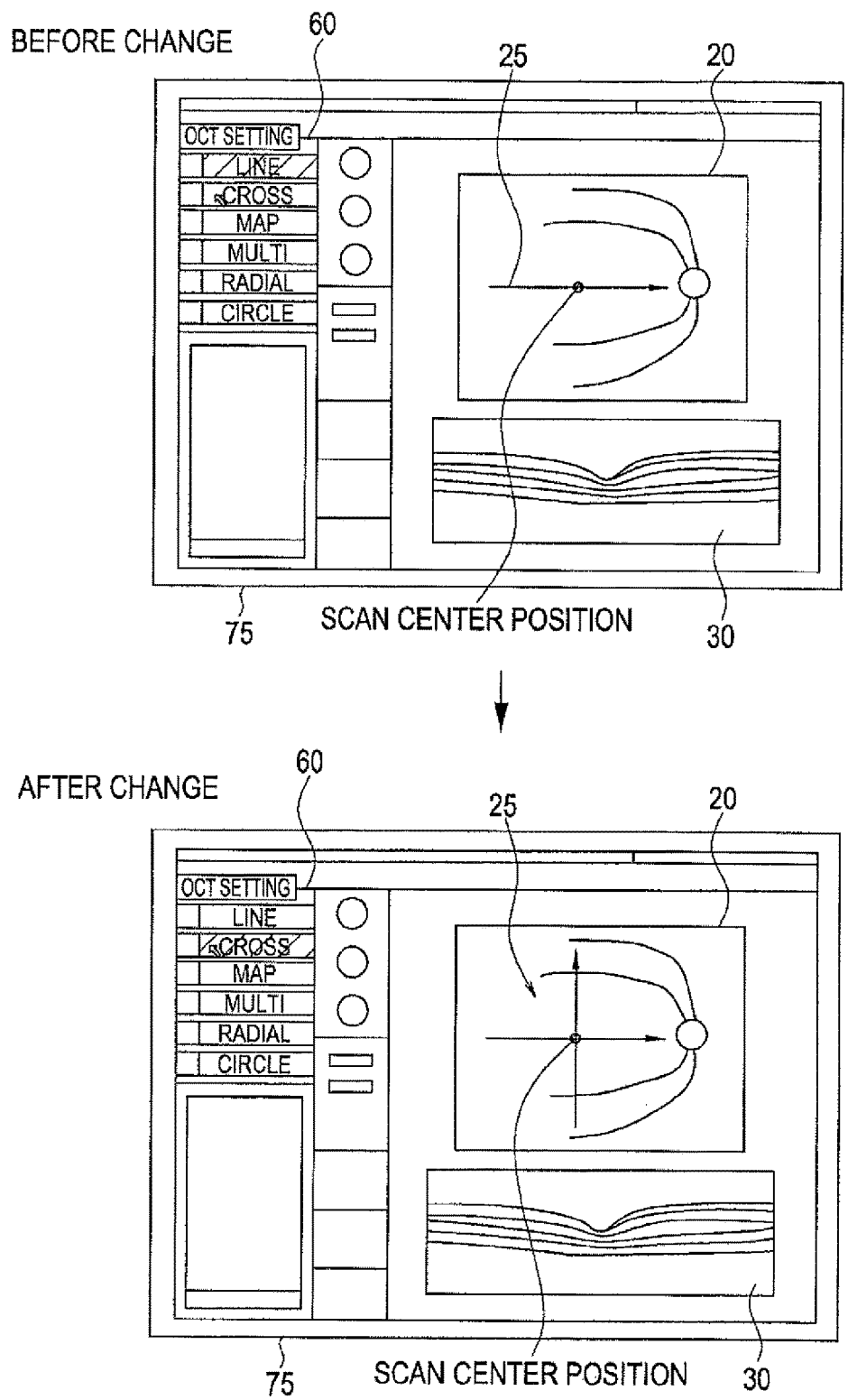

OPHTHALMOLOGIC PHOTOGRAPHING APPARATUS AND OPHTHALMOLOGIC PHOTOGRAPHING METHOD

CROSS-REFERENCE TO RELATED APPLICATION

This application claims the benefit of U.S. application Ser. No. 13/782,379 filed on Mar. 1, 2013, which is incorporated by reference and is based on Japanese Patent Application Nos. 2012-047176 and 2012-047174 filed with the Japan Patent Office on Mar. 2, 2012, the entire contents of which are hereby incorporated by reference.

BACKGROUND

1. Technical Field

The present disclosure relates to an ophthalmologic photographing apparatus and an ophthalmologic photographing method, for photographing a tomographic image of an examinee's eye.

2. Related Art

An ophthalmic optical coherence tomography (OCT) apparatus using low coherent light is known as an ophthalmologic photographing apparatus that can obtain a tomographic image of a predetermined portion (e.g., the fundus or anterior segment) of an examinee's eye noninvasively (e.g., JP-A-2008-29467).

If a tomographic image is acquired, an examiner observes a moving image of a front image of a predetermined portion of an examinee's eye on a monitor. The examiner moves a scan line indicating a tomographic image capturing position (scan position) on the moving image. Thus, the examiner sets the scan position. For example, the examiner adjusts the scan line to a portion that is considered to be a lesion on the moving image. The examiner subsequently presses a photographing start switch. Consequently, a tomographic image is photographed and captured in the apparatus.

SUMMARY

An ophthalmologic photographing apparatus includes: a photographing optical system that includes a scanning unit configured to scan an examinee's eye with measurement light to obtain a tomographic image of the examinee's eye; an observing optical system that includes a light-receiving device configured to receive reflected light from the examinee's eye to obtain a moving image of a front image of the examinee's eye based on a light-receiving signal from the light-receiving device; a user interface configured to receive a user's operation; a display configured to display the tomographic image; a memory; and a controller configured to: display, on the display, the moving image of the front image obtained by the observing optical system in real time; receive an operation signal from the user interface in response to receiving a user's setting operation for setting a scanning position of the tomographic image while the display displays the moving image; capture a still image from the moving image at the time the controller receives the operation signal and store the still image in the memory; stop displaying the moving image and display, on the display, the still image stored in the memory during the user's operation; moving a target on the still image disposed on the display in response to the user's setting operation; store scanning position information corresponding to the target in the memory at the time the user's setting operation is cancelled; stop displaying the still image and display, on the display, the moving image of the front image obtained by the observing optical system in real time when the user's setting operation is cancelled; control the scanning unit to obtain the tomographic image according to the scanning position information stored in the memory; and to correct a scanning position according to the scanning position information stored in the memory by detecting displacement between the still image stored in the memory and the moving image of the front image obtained by the observing optical system in real time after the user's setting operation is cancelled.

BRIEF DESCRIPTION OF DRAWINGS

FIG. 4 is a flowchart illustrating the operation of a scanning line setting;

FIG. 7 is a diagram illustrating a change in scan pattern on the display screen.

DETAILED DESCRIPTION

Figure 1:
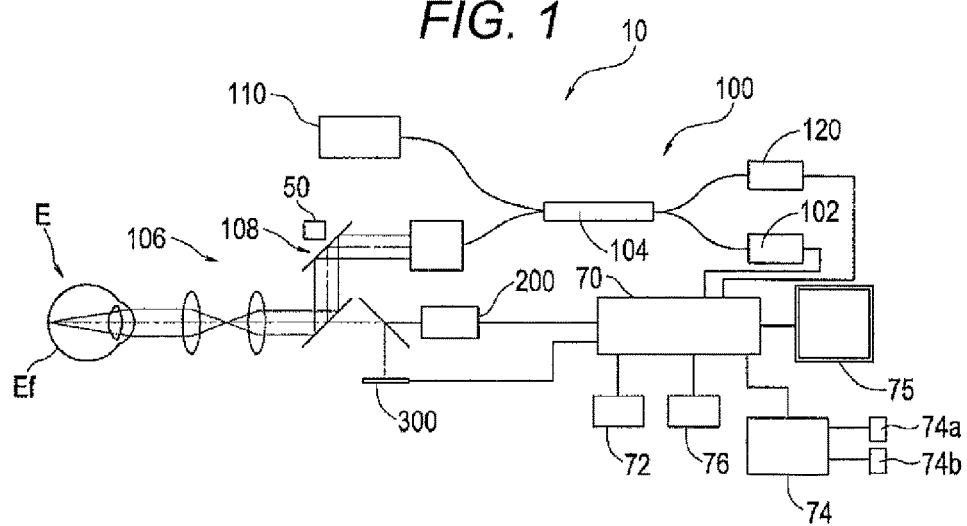
FIG. 1 is a schematic block diagram illustrating the configuration of an ophthalmologic photographing apparatus according to the example.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

A front image moves on a monitor with fine involuntary movement or breath of an examinee. Consequently, it is difficult to accurately set a scan position on an examiner's (user's) desired portion. If failing to capture an image of the desired portion, the examiner tries again. These procedures are burdens on the examiner.

An object of the present disclosure is to set, as a technical problem, providing an ophthalmologic photographing apparatus that can set an acquisition position of a tomographic image accurately and easily.

An ophthalmologic photographing apparatus according to an embodiment of the present invention (the ophthalmologic photographing apparatus) includes: a photographing optical system, including a scanning unit for scanning an examinee's eye with measurement light, for obtaining a tomographic image of the examinee's eye; an observing optical system, including a light-receiving device for receiving reflected light from the examinee's eye, for obtaining a moving image of a front image of the examinee's eye based on a light-receiving signal from the light-receiving device; a condition setting unit for setting conditions for capturing a tomographic image; and a tracking controller for performing tracking that controls the scanning unit in a manner of scanning a predetermined photographing portion of the examinee's eye based on a front image acquired by the observing optical system as well as performing tracking related to substantially the same photographing portion even in a case where the photographing condition is changed by the condition setting unit.

According to the present disclosure, it is possible to accurately and easily set a scan position relative to the examiner's desired portion.

A description will hereinafter be given of the ophthalmologic photographing apparatus according to the embodiment with reference to the drawings. FIG. 1 is a schematic block diagram illustrating the configuration of the ophthalmologic photographing apparatus according to the embodiment. In the embodiment, the axis direction of an examinee's eye (eye E) is set to be a Z direction, the horizontal direction to be an X direction, and the vertical direction to be a Y direction. Therefore, the surface direction of the fundus is the X-Y direction.

<Outline>

A description will be given of the outline of the ophthalmologic photographing apparatus according to the embodiment. An ophthalmologic photographing apparatus (optical coherence tomography device) 10 according to the embodiment includes a coherent optical system (OCT optical system) 100, an observing optical system 200, a display unit (monitor) 75, an operation input unit (operating unit) 74, and a controller (a CPU, a condition setting unit, a tracking controller, a display controller, a setting unit, and a photographing controller) 70.

The coherent optical system 100 has a scanning unit (optical scanner) 108, and a detector 120, and obtains a tomographic image of the examinee's eye. The optical scanner 108 scans the examinee's eye two-dimensionally with light emitted from a light source 102. The detector 120 detects a coherent state of measurement light emitted from the light source, and reference light.

The observing optical system 200 acquires a front image of the examinee's eye as a moving image. The observing optical system 200 has a light-receiving device. The light-receiving device receives, for example, reflected infrared light irradiating the examinee's eye, from the examinee's eye. The observing optical system 200 may obtain a front image of the examinee's eye based on a light-receiving signal from the light-receiving device. The observing optical system 200 includes, for example, an SLO or fundus camera. Moreover, the observing optical system 200 may also serve as the coherent optical system 100. In this case, a front image of the examinee's eye is acquired based on a three-dimensional image acquired by the coherent optical system 100.

If the observing optical system 200 is an SLO or fundus camera, the controller 70 aligns the positions of a front image acquired by the observing optical system 200 and a front image acquired by the coherent optical system 100 (performs matching). The front image is, for example, an OCT front image (e.g., an integral image) based on the three-dimensional image data. Consequently, the tomographic image acquired by the coherent optical system 100 is brought into correspondence with the front image acquired by the frontal-view observing optical system 200.

The operating unit 74 is operated by the examiner. The operating unit 74 may be, for example, a user interface such as a mouse 74a, a trackball, or a touchscreen.

The monitor 75 displays the front image acquired by the observing optical system 200. The monitor 75 may be, for example, a display on a PC, or a display on the ophthalmologic photographing apparatus. The monitor 75 may be a touchscreen. If the monitor 75 is a touchscreen, the monitor 75 also functions as an operating unit.

Figure 2:
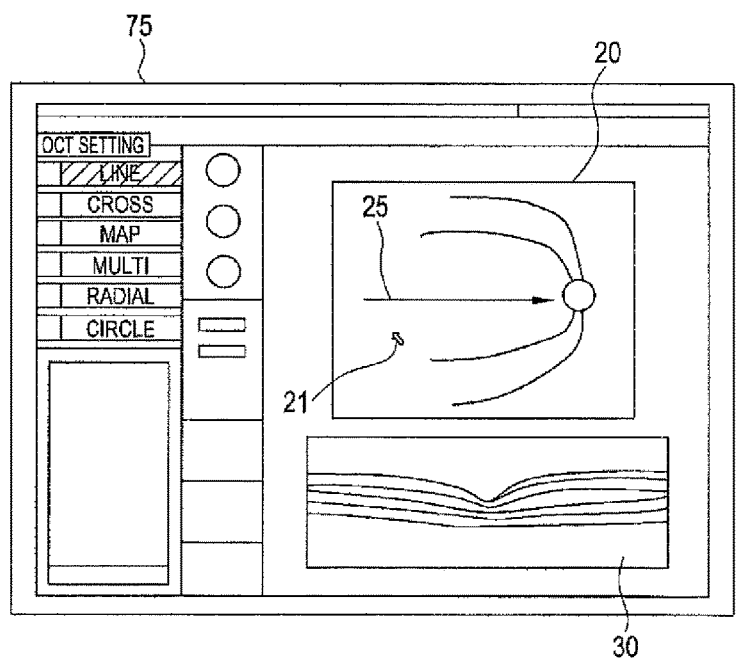
FIG. 2 is a view of an exemplary display screen on a monitor.

As illustrated in FIG. 2, the controller 70 displays a front image 20 acquired by the observing optical system 200 on the monitor 75. For example, the front image 20 acquired by the observing optical system 200 is displayed on the monitor 75 as a moving image at any time.

<Scan Position Setting>

The front image 20 acquired by the observing optical system 200 is used to select a portion to acquire a tomographic image.

The controller 70 displays, on the monitor 75, the front image 20 in the moving state, which has been acquired by the observing optical system 200. Furthermore, the controller 70 displays the front image 20 in the still state on the monitor 75. The controller 70 enables the setting of a tomographic image capturing position (acquisition position) using the front image 20 in the still state.

For example, the front image in the still state may be a still image. The front image in the moving state may be a live moving image. The controller 70 may display the front image acquired by the observing optical system 200 as a moving image on the monitor 75. Furthermore, the controller 70 may capture the front image acquired by the observing optical system 200 as a still image. The controller 70 may display the still image on the monitor 75. Furthermore, the controller 70 may be able to set a capturing position of a tomographic image, using the still image.

For example, the examiner operates the operating unit 74. In response to the operation, the operating unit 74 outputs an operation signal. The controller 70 switches a moving image displayed on the monitor 75 to a still image based on the operation signal. Furthermore, the controller 70 enables the setting of a capturing position of a tomographic image on the still image based on an operation signal from the operating unit 74. The examiner operates the operating unit 74 to specify a predetermined area in the still image. At this point, for example, the controller 70 superimposes and displays a target indicating a capturing position of a tomographic image on the still image. Furthermore, the controller 70 moves the target on the still image based on an operation signal input from the operating unit 74. Consequently, the examiner can set the capturing position (scan position by measurement light) of a tomographic image.

When the examiner specifies a predetermined area, the controller 70 sets the predetermined area specified (set) on the still image (the capturing position of a tomographic image) as a scan position by the optical scanner 108, based on an operation signal from the operating unit 74.

The controller 70 then displays a live moving image on the monitor 75 instead of the still image after completion of the setting of the scan position.

With respect to the operation of the operating unit 74, if an image to be displayed on the monitor 75 is switched between a moving image and a still image, the examiner performs a drag or click operation on the mouse 74a, for example.

If the examiner specifies the capturing position of a tomographic image, the controller 70 displays, on the monitor 75, a pointer (e.g., a cross mark, dot mark, or pen mark) that can move over the front image based on an operation signal input from the operating unit 74, for example. The controller 70 then moves the pointer (target) based on the operation signal. Consequently, the target moves over the front image. Furthermore, the controller 70 sets the capturing position (scan position by measurement light) of a tomographic image based on the operation signal.

At this point, for example, if the front image of a still image is being displayed on the monitor 75, the examiner can specify a scan position by stopping the drag operation of the mouse 74a. In this case, a position of the target on the front image on the monitor 75 of when the drag operation of the mouse 74a is stopped is set as a scan position. Moreover, if the front image of a still image is being displayed on the monitor 75, the examiner may specify a scan position by clicking the mouse 74a. The combination of a drag operation and a click operation may be used to specify a scan position.

<Tracking Control>

After the scan position is specified, the controller 70 controls the optical scanner 108 to acquire a tomographic image at the specified scan position. The controller 70 then controls (the drive of) the optical scanner 108 based on a live moving image acquired by the observing optical system 200. Consequently, the controller 70 adjusts measurement light to the scan position specified on the examinee's eye (tracks the scan position).

For example, when a scan position is specified (set), the controller 70 stores the front image used for this specification, and the information on the scan position in a memory 72. After the specification of the scan position, the controller 70 switches the display image of the monitor 75 from the still image to a live moving image.

The controller 70 detects displacement between the live moving image acquired by the observing optical system 200 and the still image used for the setting of the capturing position, by image processing. Based on the detection result, the controller 70 controls the optical scanner 108 to correct the scan position.

The displacement includes, for example, a displacement direction, rotational displacement, and the amount of displacement. The controller 70 compares the front image stored in the memory 72 and the current front image, on the live moving image, to detect the displacement between the front images by image processing.

Based on the detection result, the controller 70 controls the optical scanner 108 to correct the scan position. The controller 70 consecutively corrects the scan position. In other words, the controller 70 performs a tracking operation so as to acquire a tomographic image at the set scan position.

For example, when controlling the optical scanner 108 to correct the scan position, the controller 70 moves the position of the target (pointer) displayed on the monitor 75 to a position corresponding to the corrected scan position.

In this manner, when a scan position is set, a front image in a still state is displayed. The examiner can set the scan position using the front image in the still state. Hence, the examiner can set a scan position accurately and easily to a desired portion.

A front image in the still state may not be a still image. For example, the controller 70 may detect displacement between a live moving image acquired by the observing optical system 200 and a reference image previously acquired. In this case, the controller 70 corrects the display position of the live moving image on the monitor 75 based on the detection result. Consequently, the controller 70 may display the live moving image on the monitor 75 as a front image in the still state. In this case, an image used for tracking may be, for example, a reference image.

<Optic Disc Tracking Control>

An initial position to start a scan may be preset in accordance with a feature portion to be photographed, and the scan position may be subsequently corrected.

The controller 70 processes a previously acquired tomographic image or front image to detect a feature portion of the examinee's eye. The controller 70 sets a capturing position of a tomographic image on a front image based on the position of the detected feature portion. The controller 70 detects displacement between a live moving image acquired by the observing optical system 200 and the front image used for the setting of the capturing position of a tomographic image, by image processing. Based on the detection result, the controller 70 controls the optical scanner 108 to correct the scan position relative to the position of the feature portion. The corresponding relationship between a scan position of the optical scanner 108 and a front image is predetermined.

For example, the controller 70 may set the front image used for the setting of the capturing position of a tomographic image as a reference image. In this case, the controller 70 stores the reference image and the scan position information of an initial position in the memory 72. The controller 70 compares the reference image stored in the memory 72 and a current front image acquired by the observing optical system 200. The controller 70 detects displacement between the reference image and the current front image, by image processing. Based on the displacement, the controller 70 controls the optical scanner 108 to correct the scan position.

The above feature portions include, for example, the optic disc, the macula, and a lesioned part.

If the optic disc is set to be a feature portion, the controller 70 detects the position of the optic disc from the tomographic image or front image. The controller 70 sets a capturing position of a tomographic image on a front image based on the position of the detected optic disc. The controller 70 detects displacement between a live moving image acquired by the observing optical system 200 and the front image used for the setting of the capturing position of a tomographic image, by image processing. Based on the detection result, the controller 70 controls the optical scanner 108 to correct the scan position relative to the position of the optic disc.

The controller 70 detects a circle-shaped area apart by a predetermined distance from the center portion of the optic disc, based on the position of the detected optic disc, for example. The controller 70 may set the area as a capturing position of a tomographic image.

If the macula is set to be a feature portion, the controller 70 detects the macula from the tomographic image or front image. The controller 70 sets a capturing position of a tomographic image on a front image based on the position of the detected macula. The controller 70 detects displacement between a live moving image acquired by the observing optical system 200 and the front image used for the setting of the capturing position of a tomographic image, by image processing. Based on the detection result, the controller 70 controls the optical scanner 108 to correct the scan position relative to the position of the macula.

A feature portion may be detected, using algorithms such as edge detection and Hough transform. Moreover, a feature portion may be detected by extracting specific parts, such as a luminance change, shape, and size, of the feature portion from an image by image processing.

Consequently, there will be no need to detect the feature portion whenever the scan position is corrected. Hence, it is possible to correct the scan position speedily. Moreover, it is possible to reduce the possibility of false detection of displacement (e.g., the amount of displacement) by the misdetection of a feature portion. Hence, it is possible to correct the scan position highly accurately. Moreover, even if a photographing area is largely changed and therefore it becomes difficult to detect a feature portion, it is possible to make the correction of the scan position successful with a high probability.

<Photographing Setting Change Technique>

While the scan position is being corrected by the control of the optical scanner 108 based on displacement between front images, the examiner can change a photographing setting (photographing condition) upon photographing by operating the operating unit 74. The photographing settings include, for example, scan settings (scanning conditions) related to a scan operation of measurement light.

The controller 70 may preset a capturing position of a tomographic image on a front image displayed on the monitor 75. Furthermore, the controller 70 makes it possible for the examiner to set the scanning conditions of measurement light of when photographing a tomographic image at the set capturing position.

The controller 70 controls the optical scanner 108 based on a live moving image acquired by the observing optical system 200. Consequently, the controller 70 performs tracking on first scanning conditions.

The "tracking" indicates controlling (or consecutively controlling) the optical scanner 108 so as to be possible to scan a set (or corrected) scan position on the examinee's eye. Furthermore, tracking may include scanning the above scan position with measurement light by such control of the optical scanner 108. Furthermore, tracking may include photographing a tomographic image by such a scan. Furthermore, tracking may include displaying a photographed tomographic image on the monitor 75.

The controller 70 executes tracking on the first scanning condition. If the scanning conditions of the measurement light are subsequently changed, the controller 70 performs tracking on an acquisition position on the examinee's eye, the position being preset by the controller 70 when tracking is performed on the first scanning condition, on a second scanning condition different from the first scanning condition.

For example, in tracking on the first scanning condition, the controller 70 detects, by image processing, displacement between a live moving image acquired by the observing optical system 200 and a still image previously acquired. Based on the detection result, the controller 70 controls the optical scanner 108. Moreover, if the scanning conditions of the measurement light is changed after tracking is executed on the first scanning condition, the controller 70 detects, by image processing, displacement between a live moving image acquired by the observing optical system 200 and the still image used for tracking on the first scanning condition. Based on the detection result, the controller 70 then controls the optical scanner 108 to perform tracking on the second scanning condition.

The settable (changeable) scanning conditions include, for example, at least any of a scan pattern, the number of scanning lines, the rotation angle of a scan pattern, and a scan width.

For example, if a scan pattern is changed, the controller 70 superimposes a target indicating the scan pattern on a front image based on the scan pattern, and displays it on the monitor 75. The controller 70 changes a display pattern of the target in accordance with a change in scan pattern. For example, the target is a target indicating a scan position of measurement light. The controller 70 may correct the scan position by controlling the optical scanner 108. In this case, the controller 70 moves the display position of the target on a position on the monitor 75, the position corresponding to the corrected scan position.

In this manner, in the embodiment, it is possible to change a scanning condition during operation of tracking. Hence, when a tomographic image of the same (or substantially the same) portion is captured, even if a scanning condition is changed, it is not necessary to readjust the scan position. Hence, it is possible to acquire tomographic images of the same (or substantially the same) portion easily in various patterns. Moreover, it is possible to avoid scanning a different portion. Therefore, it is possible to scan with high accuracy. Moreover, it is possible to change a scan pattern in accordance with a photographing portion. Hence, it is highly convenient.

The number or position of at least one of a start point to start a scan of measurement light and an end point to end the scan of measurement light may be changed in accordance with a specific portion. For example, the controller 70 detects the position of the specific portion from a front image acquired by the observing optical system 200. The controller 70 sets a scan pattern of measurement light in accordance with the specific portion.

<Photographing of Tomographic Image>

After the scan position is set, photographing is performed. When the examiner operates the operating unit 74, the controller 70 captures a tomographic image captured by the coherent optical system 100 based on an operation signal from the operating unit 74 to store the tomographic image in the memory 72.

For example, upon receiving an operation signal from the operating unit 74, the controller 70 judges whether or not displacement between a live moving image and a front image used for the detection of a feature portion falls within a predetermined allowable range. The controller 70 captures a tomographic image in accordance with the judgment result and then stores the tomographic image in the memory 72.

For example, the controller 70 may make the above judgment whenever a tomographic image is captured, and determine whether or not to store the tomographic image in the memory 72. Moreover, the controller 70 may make the above judgment whenever a tomographic image is acquired, and associate the judgment result with the tomographic image to store them once in the memory 72. In this case, the controller 70 may use the judgment result associated with the tomographic image to select a tomographic image to be stored in the memory 72.

When judging that the amount of displacement does not fall within the predetermined allowable range, the controller 70 may control the optical scanner 108 such that the displacement between the live moving image and the front image used for the detection of the feature portion falls within the predetermined allowable range, and may correct the scan position. The controller 70 then captures a tomographic image of when the displacement falls within the predetermined allowable range, and then stores the tomographic image in the memory 72.

Consequently, even if a scan position is displaced after the scan position is set and before an image is captured, a tomographic image at the set scan position can be acquired with high accuracy. Moreover, a possibility to measure a different position is reduced.

Example

Hereinafter, an example of the embodiment is described with reference to the drawings. FIG. 1 is a schematic block diagram illustrating the configuration of an ophthalmologic photographing apparatus according to the example. The following description will be given of a fundus photographing apparatus (the apparatus) that photographs the fundus of the examinee's eye as an example of the ophthalmologic photographing apparatus. The ophthalmologic photographing apparatus is not limited to a fundus photographing apparatus. The ophthalmologic photographing apparatus includes an anterior segment photographing apparatus that photographs the anterior segment of the examinee's eye.

Here, the schematic configuration of the apparatus is described. The apparatus is the optical coherence tomography device (OCT device) 10 for photographing a tomographic image of a fundus Ef of the examinee's eye E. The OCT device 10 includes the coherent optical system (OCT optical system) 100, the frontal-view observing optical system 200, a fixation target projecting unit 300, and the arithmetic controller (CPU) 70.

The OCT optical system 100 irradiates the fundus with measurement light. The OCT optical system 100 detects the coherent state of the measurement light reflected by the fundus and reference light by the light-receiving device (the detector 120). The OCT optical system 100 includes an irradiation position-changing unit (e.g., the optical scanner 108 and the fixation target projecting unit 300) that changes the irradiation position of the measurement light on the fundus Ef in order to change a capturing position on the fundus Ef. The controller 70 controls the operation of the irradiation position-changing unit based on the set capturing position information. The controller 70 acquires a tomographic image based on a light-receiving signal from the detector 120.

<OCT Optical System>

The OCT optical system 100 is configured as a so-called an ophthalmic optical coherence tomography (OCT) apparatus, and captures a tomographic image of the eye E. The OCT optical system 100 allows a coupler (light splitter) 104 to split light emitted from the measurement light source 102 into measurement light (sample light) and reference light. The OCT optical system 100 allows a measuring optical system 106 to lead the measurement light to the fundus Ef of the eye E. Moreover, the OCT optical system 100 leads the reference light to a reference optical system 110. Coherent light obtained by combining the measurement light reflected by the fundus Ef and the reference light is subsequently received by the detector (light-receiving device) 120.

The detector 120 detects the coherent state of the measurement light and the reference light. In Fourier domain OCT, the spectral intensity of the coherent light is detected by the detector 120. The spectral intensity data is Fourier transformed to acquire a depth profile (A-scan signal) in a predetermined range. Fourier domain OCT includes, for example, Spectral-domain OCT (SD-OCT), Swept-source OCT (SS-OCT), and Time-domain OCT (TD-OCT).

The optical scanner 108 scans the fundus of the examinee's eye with light from the measurement light source. For example, the optical scanner 108 scans the fundus two-dimensionally (in the X-Y direction (transverse direction)) with the measurement light. The optical scanner 108 is disposed at a position that is substantially conjugated with the pupil. The optical scanner 108 has two galvanometer mirrors, for example. The reflection angles of these galvanometer mirrors are arbitrarily adjusted by a drive mechanism 50.

Consequently, it becomes possible to change a reflection (travel) direction of light flux emitted from the light source 102. Therefore, it is possible to scan the fundus in an arbitrary direction with the measurement light. Consequently, it becomes possible to change the capturing position on the fundus Ef. It is sufficient if the optical scanner 108 is configured to deflect light. A reflective mirror (a galvanometer mirror, polygon mirror, or resonant scanner), an acousto-optic modulator (AOM) that changes the travel (deflection) direction of light, or the like is used as the optical scanner 108.

The reference optical system 110 generates reference light to be combined with reflected light acquired by the reflection of the measurement light from the fundus Ef. The reference optical system 110 may be the Michelson system or Mach-Zehnder system. The reference optical system 110 includes, for example, a catoptric system (e.g., a reference mirror). The reference optical system 110 causes the catoptric system to reflect light from the coupler 104 to return the light to the coupler 104 again and leads it to the detector 120. In another example, the reference optical system 110 includes a transmission optical system (e.g., an optical fiber). The reference optical system 110 does not return the light from the coupler 104 but allows the light to pass therethrough and accordingly leads the light to the detector 120.

The reference optical system 110 includes a member for changing a difference in optical path length between measurement light and reference light by moving an optical member on a reference optical path. In the reference optical system 110, the reference mirror is moved in the optical axis direction, for example. A member to change the difference in optical path length may be disposed on a measurement optical path of the measuring optical system 106.

<Frontal-View Observing Optical System>

The frontal-view observing optical system (front image observing device) 200 is provided to obtain a front image of the fundus Ef. The observing optical system 200 has a device configuration of what is called an ophthalmic scanning laser ophthalmoscope (SLO), for example. The observing optical system 200 includes, for example, an optical scanner and a second light-receiving device. The optical scanner scans the fundus two-dimensionally with measurement light (e.g., infrared light) emitted from a light source. The second light-receiving device receives fundus reflected light via a confocal opening disposed at a position that is substantially conjugated with the fundus.

The observing optical system 200 may have the configuration of what is called a fundus camera type. Moreover, the OCT optical system 100 may also serve as the observing optical system 200. In other words, a front image may be acquired using data forming a tomographic image, the data being obtained two-dimensionally. The data include, for example, an integral image in a depth direction of a three-dimensional tomographic image, an integrated value of spectral data at the positions of X and Y, or luminance data at the positions of X and Y in a certain depth direction, and a retinal surface layer image.

<Fixation Target Projecting Unit>

The fixation target projecting unit 300 includes an optical system for guiding a direction of the visual line of the eye E. The projecting unit 300 includes a fixation target to be presented to (projected on) the eye E, and can guide the visual line of the eye E to a plurality of directions.

For example, the fixation target projecting unit 300 includes a visible light source that emits visible light, and changes a position to present the target two-dimensionally. If the direction of the visual line is changed accordingly, it leads to a change in capturing position. For example, if the fixation target is presented from the same direction as the photographing optical axis, the center portion of the fundus is set as a photographed portion. Moreover, if the fixation target is presented above the photographing optical axis, the upper part of the fundus is set as a photographed portion. In other words, a photographing portion is changed in accordance with the position of the target relative to the photographing optical axis.

Cited as the fixation target projecting unit 300 are, for example, a configuration to adjust a fixation position by adjusting the lighting state of a plurality of LEDs arranged in a matrix fashion, and a configuration to adjust a fixation position by combining a scan by an optical scanner using the light of a light source and control over the lighting up and out of the light source. Moreover, the projecting unit 300 may be an internal or external fixation light type.

<Controller>

The controller 70 controls the entire apparatus including the members 100 to 300. Moreover, the controller 70 also serves as an image processor that processes an image acquired, an image analyzer that analyzes an image acquired, and the like. The controller 70 is implemented by a general CPU (Central Processing Unit), and the like. The controller 70 analyzes the fundus Ef based on a tomographic image as indicated below.

The controller 70 acquires a tomographic image by performing image processing on a light-receiving signal output from the detector 120 of the OCT optical system 100. Furthermore, the controller 70 acquires a front image based on a light-receiving signal output from the light-receiving device of the frontal-view observing optical system 200. Moreover, the controller 70 controls the fixation target projecting unit 300 to change a fixation position.

The memory (storage unit) 72, the monitor 75, and the control unit (operating unit) 74 are electrically connected to the controller 70, respectively. The controller 70 controls a display screen of the monitor 75. An acquired fundus image is output to the monitor 75 as a still image or moving image as well as is stored in the memory 72. For example, a photographed tomographic image (e.g., a three-dimensional tomographic image), a front image, and various kinds of information on photographing such as the capturing position information of the tomographic image are recorded in the memory 72. The controller 70 controls the OCT optical system 100, the frontal-view observing optical system 200, and the fixation target projecting unit 300, based on an operation signal output from the control unit 74. The control unit 74 is connected to the mouse 74a, an operation knob 74b, and an operation knob 74c as operating members to be operated by the examiner.

The mouse 74a has a sensor, two left and right mouse buttons, and a wheel mechanism. The sensor detects a movement signal output from a main body of the mouse 74a that is moved two-dimensionally by a hand of the examiner. The mouse buttons detect a press by the hand of the examiner. The wheel mechanism is disposed between the two left and right mouse buttons. The wheel mechanism can rotate in the front and back direction.

The operation knobs 74b and 74c can rotate in the left and right direction.

The monitor 75 may be a display monitor mounted on the apparatus body, or a display monitor of a personal computer, or include both of them.

<Control Operation>

A description will be given of the control operation of the apparatus including the above configuration. The examiner instructs the examinee to fix his/her eye on the fixation target of the fixation target projecting unit 300. The examiner subsequently performs an alignment operation using an unillustrated joystick so as to locate the measurement optical axis on the pupil center of the examinee's eye while watching on the monitor 75 an anterior segment observation image captured by a camera (not shown) for anterior segment observation.

The controller 70 then controls the optical scanner 108 to scan the fundus with measurement light in a predetermined direction. The controller 70 acquires a light-receiving signal corresponding to a predetermined scan area from an output signal output from the detector 120 during the scan. The controller 70 forms a tomographic image based on the light-receiving signal. The controller 70 controls the OCT optical system 100 to acquire the tomographic image. Furthermore, the controller 70 controls the observing optical system 200 to acquire a fundus front image. The controller 70 then at any time acquires the tomographic image from the OCT optical system 100 and the fundus front image from the observing optical system 200.

FIG. 2 is a view of an example of a display screen to be displayed on the monitor 75. The controller 70 displays on the monitor 75 the front image 20 acquired by the observing optical system 200, a line (target) 25, and a tomographic image 30. The line 25 is a target representing a measuring position (capturing position) of a tomographic image on the front image 20. The line 25 is electrically displayed on the front image on the monitor 75.

The controller 70 displays on the monitor 75a pointer 21 (e.g., a cross mark, dot mark, or pen mark) that can move at any time on the monitor 75, based on an operation signal from the operating unit 74. Moreover, in the example, the examiner can set a photographing condition by performing a click or drag operation in a state where the pointer 21 is set by the mouse 74a on the front image 20. Therefore, the pointer 21 is used to specify an arbitrary position on the monitor 75.

<Setting of Scanning Line>

Figure 3A:
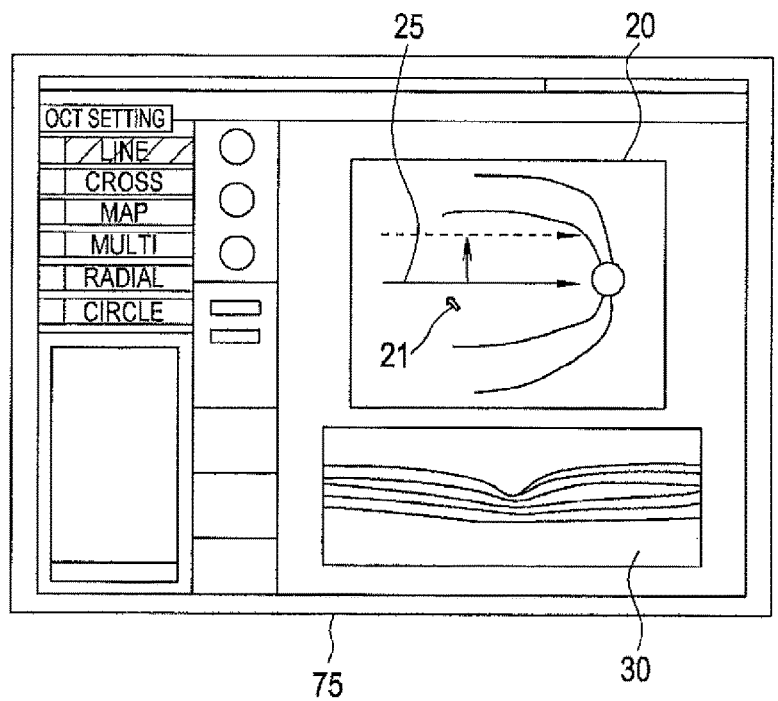
FIGS. 3A and 3B are views of displays on the screen for illustrating the setting of a scan position, respectively.
Figure 3B:
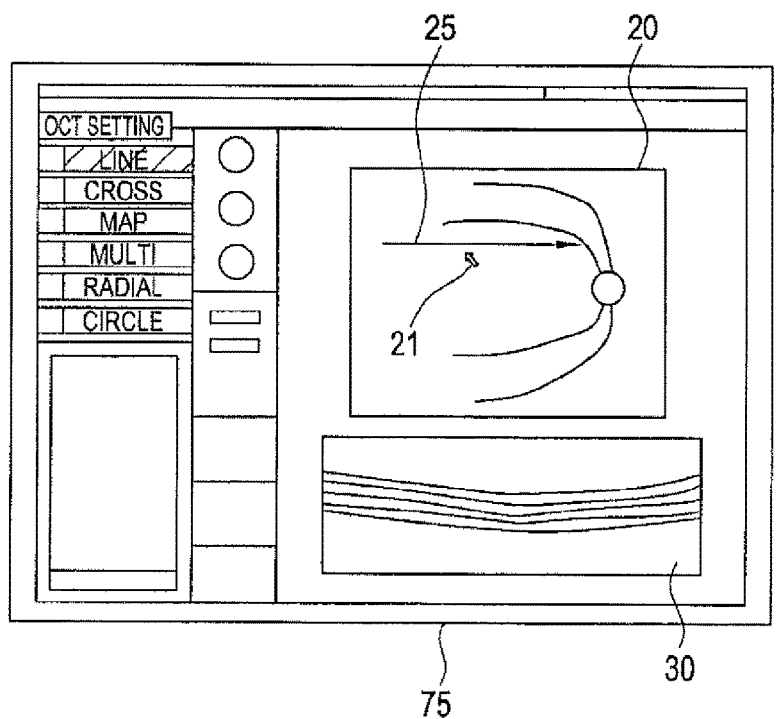

FIGS. 3A and 3B are diagrams illustrating the setting of a scan position. FIG. 4 illustrates a flowchart of the operations of setting a scanning line. If a tomographic image and a front image are displayed on the same screen, the examiner uses the front image on the monitor 75, the front image being observed in real time, to set the examiner's desired capturing position of a tomographic image. At this point, the examiner moves the line 25 on the front image by a drag operation using the mouse 74a. Consequently, the examiner sets a scan position (capturing position). If the position of the line 25 is set along the X direction, a tomographic image on the X-Z plane is captured. If the position of the line 25 is set along the Y direction, a tomographic image on the Y-Z plane is captured. Moreover, the line 25 may be configured to be possible to be set in an arbitrary shape (e.g., an oblique direction or circle) (the details are described below).

If the examiner moves the line 25 on the front image 20, the controller 70 sets a scan position at any time. The controller 70 then acquires a tomographic image at each scan position. The acquired tomographic image is then displayed on the display screen of the monitor 75 at any time. Moreover, the controller 70 changes the scan position of measurement light based on an operation signal output from the mouse 74a. The controller 70 displays the line 25 at a position on the monitor 75, the position corresponding to the changed scan position.

<Setting of Scan Position on Still Image>

Here, a method for setting a scan position (capturing position) is described. A scan position is set using a moving image or still image of the front image 20. The following description is given of the setting of a scan position using a still image. If the examiner performs a predetermined operation, the controller 70 switches a moving image of the front image 20, which is being displayed on the monitor 75, to a still image. The controller 70 enables the setting of a scan position using the still image.

For example, the controller 70 updates a front image that is sequentially acquired by the observing optical system 200. Consequently, the controller 70 displays a moving image of the front image 20 on the monitor 75. If a drag operation on the front image 20 of the moving image is started, the controller 70 captures (captures) a front image acquired by the observing optical system 200 as a still image. The controller 70 stores the still image of the front image 20 in the memory 72. The controller 70 displays the still image of the front image, which is stored in the memory 72, instead of the moving image on the monitor 75. Moreover, the controller 70 moves the line 25 to a position where the pointer 21 is displayed.

The examiner moves the mouse 74a while performing a drag operation to move the line 25 on the still image of the front image 20 (refer to FIG. 3A). Moreover, the controller 70 may change a scan pattern on the still image, the rotation angle of the scan pattern, and a scan width (scan length), based on a predetermined operation signal.

If the drag operation of the mouse 74a is cancelled (e.g., if the input of the mouse button is cancelled), the controller 70 sets, as a scan position, a portion where the line 25 is located on the still image of the front image 20 (refer to FIG. 3B). The controller 70 stores information on the scan position set using the still image, as well as the still image of the front image 20, in the memory 72.

<Acquisition of Tomographic Image>

If the setting of the scan position using the still image is completed, the controller 70 switches the front image 20 to be displayed on the monitor from the still image to a moving image. The controller 70 switches the still image of the front image displayed on the monitor 75 to a current front image acquired in real time by the observing optical system 200. Whenever a front image is acquired by the observing optical system 200, the controller 70 updates the front image.

The controller 70 acquires a tomographic image by a B-scan at the set scan position. The controller 70 controls the optical scanner 108 to obtain a tomographic image of a portion of the fundus, the portion corresponding to the display position of the line 25 on the front image 20 and accordingly scans the fundus with measurement light. The relationship between the display position of the line 25 (the coordinate position on the monitor), and the scan position of measurement light by the optical scanner 108 is predetermined. Hence, the controller 70 drives (controls) the two galvanometer mirrors of the optical scanner 108 as appropriate to scan a scan range corresponding to the set display position of the line 25 with measurement light.

<Tracking Control>

After the setting of the scan position, the controller 70 corrects the scan position whenever a front image of a moving image is updated. For example, a front image may be displaced from the front image used for the setting of the scan position due to fine involuntary movement of the examinee's eye. In this case, the scan position is corrected to acquire a tomographic image of the portion of the fundus, the portion corresponding to the scan position initially set. The controller 70 starts tracking control. In other words, after the setting of the scan position, the controller 70 uses the front image and the scan position information, which are stored in the memory 72, and corrects the scan position.

For example, the controller 70 compares the still image of the front image, which was used for the setting of the scan position, and a current front image. The controller 70 detects (computes) the direction and amount of displacement of the current front image from the still image of the front image, by image processing. For example, the controller 70 sets the still image (data) of the front image, which was used for the setting of the scan position, as a reference image. The controller 70 calculates the direction and amount of displacement between the reference image and a front image acquired in real time. Consequently, the current front image's information on the displacement from the still image is obtained.

Figure 5:
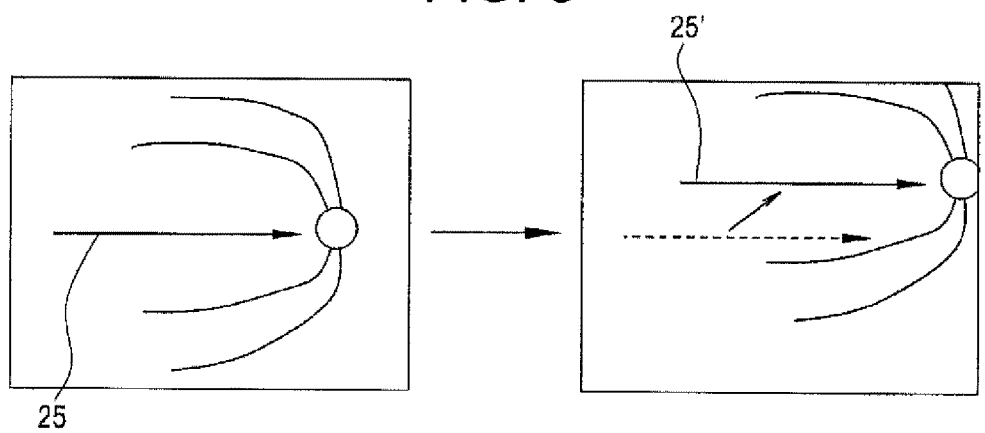
FIG. 5 is a diagram illustrating the display states of a front image before and after the correction of the scan position, respectively.

If the direction and amount of displacement are calculated as described above, the controller 70 drives (controls) the two galvanometer mirrors of the optical scanner 108 as appropriate to eliminate the displacement of the scan position. Consequently, the scan position is corrected. Moreover, as illustrated in FIG. 5, after correcting the scan position, the controller 70 displays the corrected scan position (a line 25') on a front image. As in above, even if the position of the examinee's eye deviates, the scan position is corrected. Hence, a tomographic image of the portion of the fundus, the portion corresponding to the scan position initially set, is acquired.

If an unillustrated photographing start switch (release switch) is turned on here, the controller 70 captures (captures) a still image of the tomographic image to store the still image in the memory 72. Moreover, the controller 70 displays the acquired still image of the tomographic image on the monitor 75.

As described above, in the apparatus, a moving image of the fundus being displayed on the monitor 75 is switched to a still image. The examiner can set a scan position using the still image. Hence, the examiner can set a scan position to a desired portion accurately and easily. Moreover, even if the position of examinee's eye deviates, a tomographic image of a desired portion can be reliably acquired by tracking control related to a scan position set using a still image.

If an averaged image is acquired from a plurality of tomographic images of the same (or substantially the same) portion, such control can obtain an averaged image of a desired portion. Hence, it is highly advantageous.

While the front image is being displayed as a still image, the controller 70 may consecutively display, on the monitor 75, a tomographic image in accordance with the scan position of the front image. In this case, for example, if the line 25 is moved on the still image of the front image, a tomographic image at the position of the line 25 is acquired and displayed. For example, displacement between the still image of the front image and a current front image acquired by the observing optical system 200 is detected. The scan position is corrected based on the displacement. Consequently, a tomographic image corresponding to the position of the line 25 on the still image of the front image is acquired and displayed. Consequently, it is possible to set a scan position while observing a tomographic image at the line 25. Hence, it becomes easy for the examiner to acquire a tomographic image of a desired portion. The controller 70 may acquire an averaged image using a plurality of tomographic images acquired during the setting of a scan position using a still image. Moreover, the controller 70 may display the acquired averaged image on the monitor 75 in real time.

In the example, the timing to start tracking control is set to be after the setting of a scan position. However, the timing is not limited to this, but tracking control may be started when the examiner operates the operating unit 74 to output a predetermined trigger signal after the setting of a scan position. For example, after the setting of a scan position, tracking control may be started by the examiner's setting the pointer 21 on the line 25 on the still image of the front image and performing a click operation. In this case, if a click operation is performed, the controller 70 controls the optical scanner 108, and starts the correction (tracking) of the scan position.

<Change in Scanning Condition During Tracking>

In the example, after the setting of a scan position, the examiner can change the photographing condition (e.g., the scanning condition). If a scan position is set as described above, the controller 70 corrects the scan position so as to be possible to acquire a tomographic image of a portion corresponding to the set scan position whenever the front image is updated. At this point, the examiner can change the photographing condition by operating the operating unit 74. In other words, the controller 70 can change the photographing condition during tracking control. A description will hereinafter be given of a change in photographing condition, taking a change in scanning condition as an example.

Changes in scanning condition include, for example, a change in scan length (scan width), a change in scan pattern (scan pattern), and a change in the rotation angle of the scan pattern (the rotation angle of a line to be rotated around the center of a scan).

If the first scanning condition is set, the controller 70 compares a still image of a front image, which has previously been acquired, and a current front image. The controller 70 detects (computes) the direction and amount of displacement of the current front image from the still image of the front image, by image processing. The still image is not limited to a still image switched from a moving image on the monitor 75 as in above. The still image also includes a still image of a front image acquired at certain timing.

If the direction and amount of displacement are detected, the controller 70 drives (controls) the two galvanometer mirrors of the optical scanner 108 as appropriate to eliminate the displacement of the scan position in the first scanning condition. Consequently, the scan position on the first scanning condition is corrected. Moreover, as illustrated in FIG. 5, the controller 70 displays the corrected scan position (the line 25') on the front image. If the unillustrated photographing start switch (release switch) is turned on here, the controller 70 captures (captures) a still image of a tomographic image acquired on the first scanning condition to store the still image in the memory 72. Moreover, the still image of the tomographic image is displayed on the monitor 75.

Figure 6A:
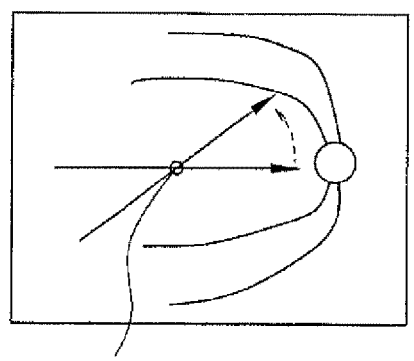
FIGS. 6A and 6B are diagrams illustrating changes in scan length and scan angle, respectively.
Figure 6B:
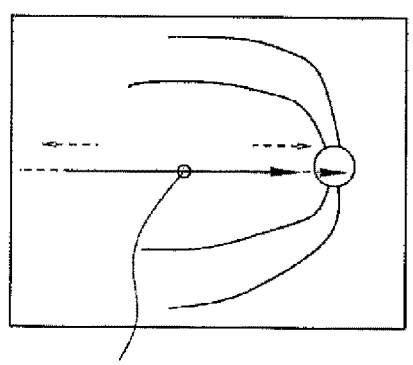

The scanning conditions may be changed during tracking (first tracking) on the above first scanning condition. In this case, the controller 70 performs tracking (second tracking) on the changed scanning condition (second scanning condition). FIGS. 6A and 6B are diagrams illustrating the changes in scan length and scan angle. The examiner changes a scan length and/or a scan angle by operating the operation knobs 74b and 74c. For example, if the examiner rotates the operation knob 74b, the controller 70 controls the optical scanner 108 to change the scan length. In this case, for example, if the operation knob 74b is rotated clockwise, the scan length becomes large, and if it is turned counterclockwise, the scan length becomes small (refer to FIG. 6A).

Moreover, if the examiner rotates the operation knob 74c, the controller 70 changes the scan angle with the center position of the scanning line (the scan center position) as the center of rotation. In this case, for example, if the operation knob 74c is rotated clockwise, the scanning line rotates clockwise with the scan center position as the center of rotation. If the operation knob 74c is rotated counterclockwise, the scanning line rotates counterclockwise (refer to FIG. 6B). Consequently, the scan angle is changed. A change(s) in scan length and/or scan angle may be changed by operating another operating unit such as a mouse.

FIG. 7 is a diagram illustrating a change in scan pattern.

FIG. 7 illustrates an example where the scan pattern is changed from a line scan to a cross scan. If the scan pattern is changed, the examiner operates the mouse 74a to select a desired scan pattern from an OCT setting field 60 displayed on the monitor 75. Consequently, the scan pattern is changed. Various scan patterns are listed in the OCT setting filed 60. The scan patterns include, for example, a cross-scan, a circle-scan, a raster-scan, and a radial-scan. Moreover, it is also possible to change the scan pattern in accordance with the photographing portion (e.g., a scan for the macula, or a scan for the optic disc). If the photographing portion is changed, the controller 70 guides the direction of the visual line of the eye E so as to be possible to photograph a desired position, by controlling the fixation target projecting unit 300.

Assume that the examiner operates the mouse 74a and selects a predetermined scan pattern in the OCT setting field 60 displayed on the monitor 75. In this case, the controller 70 changes the scan pattern to the selected scan pattern. At this point, a scan center position is preset for each scan pattern. The controller 70 changes the scan pattern such that a scan center position of a past scan pattern agrees with a scan center position of the selected scan pattern. If the scan position is not changed, a tomographic image related to the same (or substantially the same) portion on the fundus is acquired in a different scan pattern.

The controller 70 continues tracking (tracking control) even during the above change in scanning condition. If the scanning condition is changed, the controller 70 compares the same still image as the front image used for the correction (tracking) of the scan position on the first scanning condition with a current front image, for example. The controller 70 detects (computes) displacement of the current front image from the still image of the front image, by image processing. After the displacement is detected, the controller 70 drives (controls) the two galvanometer mirrors of the optical scanner 108 as appropriate to eliminate the displacement of the scan position on the changed scanning condition (second scanning condition). Consequently, the scan position on the second scanning condition is corrected.

As described above, the examiner can change the scanning condition even during tracking control. The controller 70 then adjusts the scan position so as to locate the center of a scan at the same position as the center of a scan in the photographing of the tomographic image on the first scanning condition, based on the changed scanning condition. The controller 70 subsequently continues to photograph a tomographic image. In other words, even if the scanning condition is changed, tracking control relative to the center of a scan, which was set before the change, is repeated.

If the unillustrated photographing start switch (release switch) is turned on, the controller 70 captures (captures) a still image of a tomographic image photographed on the second scanning condition to store the still image in the memory 72. Moreover, the still image of the tomographic image is displayed on the monitor 75.

In this manner, in the apparatus, the scanning condition can be changed during tracking control. Hence, even if the scanning condition is changed, it is not necessary to adjust the scan position. Hence, it is possible to acquire tomographic images of the same (or substantially the same) portion (e.g., a lesioned part) on the fundus easily in various patterns. Moreover, it is possible to avoid scanning a different portion on the fundus. Therefore, it is possible to scan with high accuracy. Moreover, it is possible to maintain the scan position at a position corresponding to the same (or substantially the same) portion of the fundus. Furthermore, it is possible to change the scan pattern in accordance with the photographing portion. Hence, it is highly convenient.

Moreover, as described above, even if the scanning condition is changed, it is possible to perform tracking using the same still image. Consequently, a positional relationship between the optical scanner 108 and the fundus is made common between the first and second scanning conditions. Hence, it is advantageous for later analysis and the like.

In the example, the example of changing the scanning condition has been given. However, the apparatus can handle any kind of change in photographing condition. For example, it is also possible to change a presentation condition of the fixation target (e.g., the pattern of the fixation target, the size of the fixation target, the fixation position) in cases such as where the fixation of the examinee is not stable during photographing. In this case, the controller 70 controls the fixation target projecting unit 300 during tracking control. Consequently, the size and/or pattern of the fixation target is/are changed.

<Photographing Operation (Semi-Auto Shot)>

When a scan position is set and the examiner presses the unillustrated photographing start switch, the controller 70 consecutively detects displacement. The controller 70 judges whether to photograph based on the detected displacement. The controller 70 controls the photographing (capture) of a tomographic image in accordance with the judgment result.

For example, if judging that displacement detected consecutively falls within the predetermined allowable range, the controller 70 automatically emits a trigger signal of the start of photographing (the capture of an image). If the trigger signal is emitted, the controller 70 photographs a tomographic image at timing when the trigger signal is emitted. The controller 70 stores the tomographic image in the memory 72 as a still image.

On the other hand, if judging that the displacement exceeds the predetermined allowable range, the controller 70 controls the optical scanner 108 to correct the scan position. If subsequently judging that the displacement (e.g., the amount of the displacement) falls within the predetermined allowable range, the controller 70 automatically emits a trigger signal of the start of photographing, and photographs a tomographic image.

In this manner, even if a scan position is set and then a front image upon photographing is displaced from a front image upon setting of the scan position before a tomographic image is captured (if there is displacement), it is possible to photograph a tomographic image of a portion of the fundus, the portion corresponding to the set scan position, with high accuracy. Moreover, a possibility to photograph a tomographic image of a different portion is reduced.

<Modification>

A description will hereinafter be given of a modification according to the example. In the modification, a description will be given, taking, as an example, a case where an initial position to start a scan is set in accordance with a feature portion of the examinee's eye. In the following description, the optic disc portion (optic disc) is given as an example of a feature portion.

<Detection of Position of Optic Disc>

The controller 70 controls the observing optical system 200 to acquire a front image including the optic disc. The controller 70 detects the position of the optic disc in the acquired front image.

In the front image, the optic disc indicates a luminance change (light/dark) that is different from another fundus portion. The controller 70 detects a portion having a lower luminance level than a predetermined level or a higher luminance level than a predetermined level, by image processing. Consequently, the controller 70 identifies the position of the optic disc. When identifying the position of the optic disc, the controller 70 detects an outer edge of the optic disc by edge detection based on a luminance change, for example.

The controller 70 calculates the center position of the optic disc in the front image. The controller 70 obtains, for example, the center coordinates of the optic disc by making circle approximation of the outer edge of the optic disc, and detecting (calculating) the center coordinates of the approximate circle. The controller 70 handles the detected center coordinates of the approximate circle as the center coordinates of the optic disc.

<Correction of Scan Position (Manual Change in Optic Disc Detection Position)>

After detecting the position of the optic disc, the controller 70 sets an initial position of a scan position. The controller 70 sets, as the initial position, a scan position that the center position of the optic disc agrees with the scan center position. The controller 70 stores, in the memory 72, a still image of the front image used for the detection of the optic disc (the detection of the position of the optic disc), and information on the scan position set using the front image.

When the initial position is set, the controller 70 photographs a tomographic image of a portion of the fundus, the portion corresponding to the initial position, and displays the tomographic image as well as a front image on the monitor 75. Moreover, the controller 70 corrects the scan position whenever the front image of a moving image is updated after the setting of the initial position. In other words, the controller 70 starts tracking control. After the setting of the scan position, the controller 70 uses the front image and the scan position information, which are stored in the memory 72, and corrects the scan position.

A description will be given of the correction of the scan position. Firstly, the controller 70 compares the front image used for the detection of the optic disc and stored in the memory 72, and a current front image. The controller 70 detects (computes) the direction and amount of displacement of the current front image from the front image used for the detection of the optic disc, by image processing.

The controller 70 sets the front image (or its data) used for the detection of the optic disc, as a reference image. The controller 70 calculates displacement between the reference image and a current front image acquired in real time. Consequently, the current front image's information on the displacement from the front image used for the detection of the optic disc is obtained.

After the displacement information is acquired, the controller 70 drives (controls) the two galvanometer mirrors of the optical scanner 108 as appropriate to correct the above displacement. Consequently, the scan position is corrected.

In this manner, in the modification, the position of a feature portion (e.g., the optic disc) in a front image is detected in advance by image processing. The controller 70 corrects the scan position using relative displacement between this front image and a front image later acquired. Consequently, the controller 70 does not need to detect the feature portion whenever a front image is acquired. Hence, the controller 70 can correct the scan position speedily.

Moreover, it is possible to reduce the possibility of false detection of displacement by the misdetection of the feature portion. Hence, it is possible to correct the scan position with high accuracy. Moreover, even if a part of the feature portion cannot be detected since a fundus image has moved largely, it is possible to make the correction of the scan position successful with a high probability.

If the examiner desires to modify the scan position relative to the position of a feature portion, the controller 70 may switch a front image that is being displayed on the monitor 75 from a moving image to a still image in accordance with an operation signal from the examiner (the operating unit 74), as described above. The controller 70 may modify (set) the scan position relative to the position of the feature portion using this still image (refer to <Setting of Scan Position on Still Image>, <Acquisition of Tomographic Image>, and <Tracking Control>).

In other words, tracking control based on the setting of a scan position on a still image and tracking control based on the detection of a feature portion can be used in combination. For example, if the displacement of the position of a feature portion (detection result) is confirmed from an observing image, the examiner switches the display mode of a front image to a still image. The examiner (the controller 70) then modifies the scan position relative to the position of the feature portion. Tracking control using the modified scan position and the still image is subsequently performed.

Also in the modification, as described above, it is also possible to change the photographing condition during tracking control.

<Displacement Detection Method>

Methods for detecting displacement between two images include various image processing methods (e.g., a method using various correlation functions, a method using a Fourier transform, and a method based on the matching of a feature point).

For example, a predetermined reference image (e.g., a past front image) or a target image (a current front image) is shifted one pixel by one pixel. The reference image and the target image are subsequently compared. Displacement between both data of when both image data are most coincident with each other (when the correlation is the strongest) may be detected. Moreover, it is also possible to use a method for extracting a feature point that is common between the predetermined reference image and the target image, and detecting the displacement of the extracted feature point.

Moreover, a function for obtaining displacement between two images may be a phase-only correlation function. If this function is used, each image is Fourier transformed first. Consequently, the phase and amplitude of each frequency component is obtained. The obtained amplitude component may be normalized to size 1 with respect to each frequency component. Next, the phase difference of each frequency is calculated between the two images. An inverse Fourier transform is subsequently performed on them.

Here, if there is no displacement between the two images, only cosine waves are added. Hence, a peak appears at an origin point position (0, 0). Moreover, if there is displacement, a peak appears at a position corresponding to the displacement. Hence, the presence or absence of displacement between the two images, and the position of the displacement are obtained by obtaining the detection position of the peak. According to the method, it is possible to detect displacement of a front image with high accuracy and in short time.

With respect to the operation of the operating unit 74, for example, if a moving image displayed on the monitor 75 is switched to a still image, the examiner changes a moving image and a still image by a drag operation, a click operation, or the like of the mouse 74a.

For example, if a scan position is specified, for example, the controller 70 displays, on the monitor 75, a pointer (e.g., a cross mark, dot mark, or pen mark) that can move over a front image based on an operation signal input from the operating unit 74. By moving the pointer, the target (scan position) is moved on the front image to set the scan position of measurement light.

At this point, it is cited, for example, in a state where a front image displayed on the monitor 75 is set to be a still image by a drag operation of the mouse 74a that the examiner stops the drag operation of the mouse 74a to specify the scan position. When the drag operation of the mouse 74a is stopped, an area where the target on the front image on the monitor 75 is located is set as the scan position. Moreover, in a state where a front image displayed on the monitor 75 is set to be a still image by a click operation of the mouse 74a, the scan position may be specified by a click operation. Naturally, a drag operation and a click operation may be combined.

Moreover, in tracking control, the controller 70 may correct the scan position whenever a front image of a moving image is updated after the setting of the scan position. For example, if a front image is displaced from the scan position due to fine involuntary movement of the examinee's eye, and the like, the scan position is corrected to acquire a tomographic image at the same position as the position to which the scan position was set. The controller 70 starts tracking control. After the setting of the scan position, the controller 70 uses a front image and scan position information, which are stored in the memory 72, to correct the scan position.

In a change in scanning conditions in a tracking state (a change in scanning conditions during tracking), the condition of a scan can be changed during tracking control and accordingly it is not necessary to readjust the scan position when any change occurs in the scanning conditions. Hence, it is possible to easily acquire, for example, tomographic images of the same portion (e.g., a lesioned part) on the fundus in various patterns, which does not become trouble. Furthermore, it is possible to avoid the setting of a scan position of a different portion on the fundus, and it is possible to carry out a scan with high accuracy. Furthermore, it is possible to change the scan pattern in accordance with the photographing portion without the scan position being displaced from the same portion; accordingly, it is advantageous.

In the photographing operation (semi-auto shot), even if a scan position is displaced after the scan position is set and before an image is acquired, a tomographic image at the set scan position can be acquired with high accuracy. In addition, a possibility to measure a different position is reduced.

In the modification, furthermore, the scan position is corrected using relative displacement between a front image where the position of a feature position (e.g., the optic disc) has previously been detected by image processing, and a front image later acquired and accordingly it is not necessary to detect the feature portion whenever a front image is acquired. Therefore, the scan position can be corrected speedily. If the examiner desires to modify the scan position relative to the feature portion, the controller 70 may switch a moving image of a front image on the monitor 75 to a still image in accordance with an operation signal from the examiner, and set the scan position relative to the feature portion on the still image, as described above (refer to <Setting of Scan Position on Still Image>, <Acquisition of Tomographic Image>, and <Tracking Control>). In other words, tracking control based on the setting of a scan position on a still image and tracking control based on the detection of a feature portion can be used in combination. For example, if a state where displacement has occurred in the detection result of the feature portion is confirmed from an observing image, the examiner switches the front image to a still image and modifies the scan position relative to the feature portion. Tracking control is subsequently performed using the modified scan position and the still image.

Moreover, the ophthalmologic photographing apparatus according to the embodiment may be the following first to eighteenth ophthalmologic photographing apparatuses. The first ophthalmologic photographing apparatus includes: an imaging optical system, including a scanning unit for scanning an examinee's eye with measurement light emitted from a light source, for obtaining a tomographic image of an examinee's eye; an observing optical system, including a light-receiving device for receiving reflected light from the examinee's eye, for obtaining a moving image of a front image of the examinee's eye based on a light-receiving signal from the light-receiving device; a display controller for displaying the front image in a moving state, the front image being acquired by the observing optical system, on a monitor while displaying the front image in a still state on the monitor, as well as making possible setting of an acquisition position of the tomographic image on the front image displayed in the still state; and a drive controller for controlling the scanning unit to acquire a tomographic image at the acquisition position set on the still image in the still state.

In accordance with the second ophthalmologic photographing apparatus in the first ophthalmologic photographing apparatus, the display controller switches the front image displayed in a moving state on the monitor based on an operation signal input from an operation input unit as well as can set an acquisition position of the tomographic image on the front image displayed in the still state based on an operation signal input from the operation input unit.

In accordance with the third ophthalmologic photographing apparatus in the first ophthalmologic photographing apparatus, the display controller switches the front image displayed in the still state on the monitor to a live moving image upon the setting being complete on the front image displayed in the still state. In accordance with the fourth ophthalmologic photographing apparatus in the first ophthalmologic photographing apparatus, the drive controller controls the drive of the scanning unit based on a live moving image acquired by the observing optical system, and tracks the measurement light to the acquisition position on the examinee's eye, the acquisition position being set on the front image displayed in the still state.

In accordance with the fifth ophthalmologic photographing apparatus in the first ophthalmologic photographing apparatus, the drive controller detects, by image processing, displacement between a live moving image acquired by the observing optical system and the front image used for the setting of the acquisition position in the still state, controls the drive of the scanning unit based on the detection result, and corrects a scan position. In accordance with the sixth ophthalmologic photographing apparatus in the first ophthalmologic photographing apparatus, the display controller superimposes and displays a target indicating the acquisition position of a tomographic image on the front image displayed in the still state as well as moves the target on the front image based on an operation signal input from the operation input unit, and can set the scan position of the measurement light.

In accordance with the seventh ophthalmologic photographing apparatus in the first ophthalmologic photographing apparatus, if a scan position is corrected, the display controller changes a display position of a target to a position corresponding to the corrected scan position. In accordance with the eighth ophthalmologic photographing apparatus in the first ophthalmologic photographing apparatus, the observing optical system includes a light-receiving device for irradiating the examinee's eye with infrared light and receiving reflected light from the examinee's eye, and obtains the front image of the examinee's eye based on a light-receiving signal from the light-receiving device.

In accordance with the ninth ophthalmologic photographing apparatus in the first ophthalmologic photographing apparatus, the display controller captures the front image acquired by the observing optical system as a still image to display the still image as the front image in the still state on the monitor as well as can set the acquisition position of the tomographic image on the still image.

In accordance with the tenth ophthalmologic photographing apparatus in the first ophthalmologic photographing apparatus, the display controller detects displacement between a live moving image acquired by the observing optical system and a reference image, and corrects a display position of the live moving image on the monitor based on the detection result to display the live moving image on the monitor as the front image in the still state.

The eleventh ophthalmologic photographing apparatus in the first ophthalmologic photographing apparatus includes a setting unit for processing the tomographic or front image previously acquired to detect a feature portion of the examinee's eye by image processing, and setting an acquisition position of a tomographic image on a front image based on a position of the detected feature portion, wherein the drive controller detects, by image processing, displacement between a live moving image acquired by the observing optical system and the front image where the acquisition position of the tomographic image has been set, controls the drive of the scanning unit based on the detection result, and corrects a scan position relative to the feature position.

In accordance with the twelfth ophthalmologic photographing apparatus in the eleventh ophthalmologic photographing apparatus, the setting unit sets the front image where the acquisition position of the tomographic image has been set, as a reference image, and stores, in a storage unit, the reference image and information on the set acquisition position of the tomographic image, and the drive controller compares the reference image stored in the storage unit and a current front image acquired by the observing optical system, detects displacement of the current front image from the reference image by image processing, controls the drive of the scanning unit based on the detection result, and tracks the measurement light to the acquisition position on the examinee's eye, the acquisition position being set by the setting unit.

In accordance with the thirteenth ophthalmologic photographing apparatus in the eleventh ophthalmologic photographing apparatus, the setting unit detects the optic disc from the tomographic or front image, and sets an acquisition position of a tomographic image on a front image based on a position of the detected optic disc, and the drive controller detects, by image processing, displacement between a live moving image acquired by the observing optical system and the front image where the acquisition position of a tomographic image has been set, controls the drive of the scanning unit based on the detection result, and corrects a scan position relative to the optic disc.

In accordance with the fourteenth ophthalmologic photographing apparatus in the thirteenth ophthalmologic photographing apparatus, the setting unit sets a circle-shaped area apart by a predetermined distance from a center position of the optic disc as an acquisition position of a tomographic image based on the position of the detected optic disc.

In accordance with the fifteenth ophthalmologic photographing apparatus in the eleventh ophthalmologic photographing apparatus, the setting unit detects the macula from the tomographic or front image, and sets an acquisition position of a tomographic image on a front image based on a position of the detected macula, and the drive controller detects, by image processing, displacement between a live moving image acquired by the observing optical system and the front image where the acquisition position of a tomographic image has been set, controls the drive of the scanning unit based on the detection result, and corrects a scan position relative to the macula.

The sixteenth ophthalmologic photographing apparatus in the eleventh ophthalmologic photographing apparatus includes a photographing controller for capturing a tomographic image acquired by a coherent optical system based on an operation signal from an operation input unit, and storing the tomographic image in a storage unit. In accordance with the seventeenth ophthalmologic photographing apparatus in the sixteenth ophthalmologic photographing apparatus, after an operation signal from the operation input unit is input, the photographing controller judges whether or not displacement between the live moving image and the front image where the acquisition position of a tomographic image has been set falls within a predetermined allowable range, captures the tomographic image using the judgment result, and stores the tomographic image in the storage unit.

In accordance with the eighteenth ophthalmologic photographing apparatus in the seventeenth ophthalmologic photographing apparatus, the drive controller controls the drive of the scanning unit such that the displacement between the live moving image and the front image where the acquisition position of a tomographic image has been set falls within the predetermined allowable range, and corrects the scan position, and the photographing controller captures the tomographic image of when the displacement falls within the predetermined allowable range, and stores the tomographic image in the storage unit.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmologic photographing apparatus comprising:
    a photographing optical system that includes an optical scanner configured to scan an examinee's eye with measurement light to obtain a tomographic image of the examinee's eye;
    an observing optical system that includes a light-receiving device configured to receive reflected light from the examinee's eye to obtain a moving image of a front image of the examinee's eye based on a light-receiving signal from the light-receiving device;
    a user interface configured to receive a user's operation;
    a display configured to display the tomographic image;
    a memory; and
    a controller configured to:
    display, on the display, the moving image of the front image obtained by the observing optical system in real time;
    receive an operation signal from the user interface in response to receiving a user's setting operation for setting a scanning position of the tomographic image while the display displays the moving image;
    capture a still image from the moving image at the time the controller receives the operation signal and store the still image in the memory;
    stop displaying the moving image and display, on the display, the still image stored in the memory during the user's operation;
    move a target on the still image disposed on the display in response to the user's setting operation, the user's setting operation including the user specifying an area in the still image;
    store scanning position information corresponding to the target in the memory at the time the user's setting operation is cancelled;
    stop displaying the still image and display, on the display, the moving image of the front image obtained by the observing optical system in real time when the user's setting operation is cancelled;
    control the optical scanner to obtain the tomographic image according to the scanning position information stored in the memory; and to correct a scanning position according to the scanning position information stored in the memory by detecting displacement between the still image stored in the memory and the moving image of the front image obtained by the observing optical system in real time after the user's setting operation is cancelled.

2. The ophthalmologic photographing apparatus according to claim 1, wherein the user's setting operation includes a drag operation of dragging the target on the still image to move the target on the still image.

3. The ophthalmologic photographing apparatus according to claim 2, wherein
    while the target is dragged, the controller displays the still image on the display, and
    when dragging of the target is cancelled, the controller stops displaying the still image and displays, on the display, the moving image of the front image.

4. A method of controlling an ophthalmologic photographing apparatus which includes: a photographing optical system that includes an optical scanner configured to scan an examinee's eye with measurement light to obtain a tomographic image of the examinee's eye; an observing optical system that includes a light-receiving device configured to receive reflected light from the examinee's eye to obtain a moving image of a front image of the examinee's eye based on a light-receiving signal from the light-receiving device; a user interface configured to receive a user's operation; a display configured to display the tomographic image; and a memory, the method comprising:

displaying, on the display, the moving image of the front image obtained by the observing optical system in real time;

receiving an operation signal from the user interface in response to receiving a user's setting operation for setting a scanning position of the tomographic image while the display displays the moving image;

capturing a still image from the moving image at the time the controller receives the operation signal and store the still image in the memory;

stopping displaying the moving image and display, on the display, the still image stored in the memory during the user's operation;

moving a target on the still image disposed on the display in response to the user's setting operation, the user's setting operation including the user specifying an area in the still image;

storing scanning position information corresponding to the target in the memory at the time the user's setting operation is cancelled;

stopping displaying the still image and display, on the display, the moving image of the front image obtained by the observing optical system in real time when the user's setting operation is cancelled;

controlling the optical scanner to obtain the tomographic image according to the scanning position information stored in the memory; and to correct a scanning position according to the scanning position information stored in the memory by detecting displacement between the still image stored in the memory and the moving image of the front image obtained by the observing optical system in real time after the user's setting operation is cancelled.

5. The method according to claim 4, wherein the user's setting operation includes a drag operation of dragging the target on the still image to move the target on the still image.

6. The method according to claim 5, wherein while the target is dragged, the controller displays the still image on the display, and when dragging of the target is cancelled, the controller stops displaying the still image and displays, on the display, the moving image of the front image.

\* \* \* \* \*